(12) United States Patent
Komissarova et al.

(10) Patent No.: US 8,367,730 B2
(45) Date of Patent: Feb. 5, 2013

(54) COMPOSITION OF AMINO ACIDS FOR SUBLINGUAL APPLYING FOR ENHANCED SKIN INTEGUMENT REPIGMENTATION IN VITILIGO AND METHOD OF ITS ADMINISTRATION

(75) Inventors: Irina Alekseevna Komissarova, Moscow (RU); Yaroslav Ryurikovich Nartsissov, legal representative, Moscow (RU); Irina Markovna Korsunskaya, Moskovskaya (RE); Yaroslav Ryurikovich Nartsissov, Moscow (RU)

(73) Assignee: Nekimmercheskoe Uchrezhdenie "Nauchno-Issledovatel'skij Institut Tsitokhimii I Molekulyarnoyj Farmakologii", Moscow (RU)

( * ) Notice: Subject to any disclaimer, the term of this patent is extended or adjusted under 35 U.S.C. 154(b) by 42 days.

(21) Appl. No.: 13/097,045

(22) Filed: Apr. 28, 2011

(65) Prior Publication Data
US 2011/0251279 A1  Oct. 13, 2011

Related U.S. Application Data

(63) Continuation of application No. PCT/RU2009/000701, filed on Dec. 18, 2009.

(30) Foreign Application Priority Data

Dec. 26, 2008  (EA) .................................. 200900146

(51) Int. Cl.
*A61K 31/195* (2006.01)
(52) U.S. Cl. ........................ 514/561; 514/562; 514/565
(58) Field of Classification Search .................. 514/561, 514/562, 565
See application file for complete search history.

(56) References Cited

U.S. PATENT DOCUMENTS
2004/0258717 A1  12/2004  Sauermann

FOREIGN PATENT DOCUMENTS
RU  2096034 C1  11/1997

OTHER PUBLICATIONS
Korsunskaya, "Vitiligo. Genetic and metabolic features of the disease, strategy of treatment Thesis of the dissertation for a degree the Doctor of Medicine on specialties 14.00.25 and 14.00.11", 2004, Moscow.
Schallreuter et al, "From basic research to the bedside: efficacy of topical treatment with pseudocatalase PC-KUS in 71 children with vitiligo", International Journal of Derm. Jul. 2008, 47(7): 743-53.
Proshutinskaya, "Selective phototherapy of children with vitiligo with regard to the role of immune changes, Thesis of the dissertation for a degree the Doctor of Medicine on specialty 14.00.11", 2004, p. 19, Moscow.
Voloshin, "Clinical and pharmacological characteristics of combining vitiligo treatment with the use of photochemotherapy and reflexotherapy methods, Thesis of the dissertation for a degree the Doctor of Medicine on specialties 14.00.25 and 14.00.11", 2006, Volgograd.
Koshevenko, "Vitiligo Phototherapy Justification, Characteristics, Clinical Performance" Lecture, Non-State Educational Institution Akademiya Kosmetologii, Moscow.
Orecchia et al., "Cystine in the treatment of vitiligo" Gital Dermatol Venereol. Nov.-Dec. 1998; 124 (11-12):529-31, abstract.
Ishikawa et al., "Combination of Amino Acids Reduces Pigmentation in B16F0 Melanoma Cells", Biol Pharm Bull. Apr. 2007, 30(4):677-81.
Reish et all, "Tyrosinase Inhibition Due to Interaction of Homocyst(e)ine with Copper: the Mechanism for Reversible Hypopigmentation in Homocystinuria due to Cystathionine Beta-Synthase Deficiency", Am J Hum Genet. Jul. 1995;57 (1):127-32.
International Search Report from corresponding application PCT/RU2009/000701, filed on Dec. 18, 2009, mailed on May 20, 2010.

*Primary Examiner* — Raymond Henley, III
(74) *Attorney, Agent, or Firm* — Patentbar International, P.C.

(57) ABSTRACT

The task of this invention is in use of composition containing natural metabolites—amino acids, and in method of its administration which make it possible to increase skin repigmentation through sulfurcontaining compounds rise and activation of endogenic metabolic reactions, and to get persistent normalization of melanogenesis thus improving skin integument and as a consequence patient's quality of life.
Composition includes L cystine, L glutamic acid and glycine in the following quantity, mg:

| L cystine | 85 ± 10%, |
| L glutamic acid | 85 ± 10%, |
| Glycine | 85 ± 10% |

The amino acid composition mentioned above must be administered 3 times a day for 5 weeks independent of meal in accordance with method of increase of skin integument repigmentation in vitiligo. The course can be repeated in 4-5 weeks.

5 Claims, No Drawings

COMPOSITION OF AMINO ACIDS FOR SUBLINGUAL APPLYING FOR ENHANCED SKIN INTEGUMENT REPIGMENTATION IN VITILIGO AND METHOD OF ITS ADMINISTRATION

RELATED APPLICATIONS

This Application is a Continuation application of International Application PCT/RU2009/000701 filed on Dec. 18, 2009, which in turn claims priority to Eurasian patent application EA200900146 filed on Dec. 26, 2008 entitled, both of which are incorporated herein by reference in their entirety.

FIELD OF THE INVENTION

The invention relates to medicine, ortho-molecular medicine, pharmaceuticals, nutrition, biochemistry of amino acids, in particular to composition of amino acids for sublingual applying for enhanced repigmentation of skin integument in vitiligo and method of its administration.

BACKGROUND OF THE INVENTION

Individuals of various ethnicities and races may suffer from chronic dermatosis (vitiligo) characterized by appearance of depigmentation focuses on the skin. Histologic studies of such focuses show absence or reduction of melanine.

Etiology, pathogenesis and vitiligo treatment has been one of the unresolved issues of dermatology. Wide spread of vitiligo in many ethnic groups and areas, its significant influence on psychosocial status, lack of efficient methods of treatment and information about possible interrelation of vitiligo pathogenesis and skin melanoma indicate to topicality of fundamental studies, research and elaboration of new means contributing to normalization of melanogenesis.

Given views of the role of vitiligo genetic disposition, immunopathology (I. M Karsunskaya., Vitiligo Genetic and metabolic features of the disease, treatment method. Abstract for a thesis for a doctor's of medicine degree, Moscow, 2004) of biochemical disorders in the form of decrease of catalase and tiriodin—reductase activity (K.U. Schallreuter, The society for Investigate Dermatology, International journal of derm. 2008, July 47(7): 743-53) inspiring oxidative stress, treatment methods have symptomatic character. They are not efficient enough, may cause traumas and they are quite limited because of adverse by-effects.

There is known vitiligo treatment method characterized by use of ultraviolet radiation, ultraviolet radiation with reflexotherapy and photosensitizing drugs in particular, for melanogenesis stimulation. (D. V. Proshutinskaya, Selective phototherapy of vitiligo-ill children taking into account role of immune changes, abstract of a thesis for a candidate of medicine, Moscow, 2004, p. 19; R. N. Voloshin., Clinico-pharmacologic features of complex vitiligo treatment by methods of psoralen ultraviolet radiation of A band) and reflexotherapy, abstract of a thesis for doctor's of medicine degree, 14.0025, Volgograd, 2006; U. N. Koshevenko, Phototherapy of vitiligo: substantiation, characteristics, clinical effect, Russian journal of skin and veneral diseases, 2001, No3., p. 58-66). Contraindications to such exposures in most of coexistent diseases, total and local side effects including increase possibility of squamous cell carcinoma formation restrict using long-wave ultraviolet rays.

For immune disorders correction there are used polyoxidonium and amixin. However administration of the mentioned drugs does not ensure full, intense and persistent repigmentation. Polyoxidonium is administered in the form of injections which is attended by undesirable everyday (10-week) injury of skin integuments and risk of local infection Amixin is administered only since 14 years of age and is contraindicated in affected thyroid.

SUMMARY OF THE INVENTION

The task of this invention is in use of composition containing natural metabolites—amino acids, and in method of its administration which make it possible to increase skin repigmentation through sulfurcontaining compounds rise and activation of endogenic metabolic reactions, and to get persistent normalization of melanogenesis thus improving skin integument and as a consequence patient's quality of life.

DETAILED DESCRIPTION OF THE INVENTION

The given task is accomplished by composition of amino acids for sublingual applying for enhanced skin integument repigmentation in vitiligo which includes L cystine, L glutamic acid and glycine in the following quantity, mg:

| | |
|---|---|
| L cystine | 85 ± 10%, |
| L glutamic acid | 85 ± 10%, |
| Glycine | 85 ± 10% |

The amino acid composition mentioned above must be administered 3 times a day during 5 weeks independent of meal in accordance with method of increase of skin integument repigmentation in vitiligo.

The course can be repeated in 4-5 weeks. Composition can be administered in the form of a tablet or powder obtained by tablet porphyrizing.

Composition in the form of a tablet contains additionally ether of cellulose and stearate as excipients in the quantity of 1%-10% of tablet weight for each agent.

Realization of Invention

For quite a long time there have been conducted studies of medical possibilities of amino acids composition of L cystine, L glutamic acid and glycine. Amino acids composition of L cystine, L glutamic acid and glycine is known to be used in components mass ratio 1:1:1 and with quantity content of 0.1 g. for each component as a means inducing glutathione biosynthesis, glutathione transferase activity and having detoxifying, antiradiation and antihypoxic action (RU 2096034 Cl, IPC 6 A61K 31/195, 1997).

However as a means of persistent repigmention in vitiligo achievement amino acids composition of L cystine, L glutamic acid and glycine in the form of monoimpact was first offered by the authors of the present invention Irina. Alekseevna Komissarova, Irina Markovna Korsunskaya and Yaroslav Riurikovich Nartsissov. Clinical research and estimation of medicine efficiency were carried out through mediation of Marina Alexandrovna Gornostaeva and Ekaterina Viktorovna Zhavoronkova.

After the course of administration of elaborated composition there is reached an effect which induces changes in color of depigmentation focuses, appearance of pigmented areas akin to disseminations. Such result could not be achieved in such short terms and by use of other known methods earlier.

Further pigmentation augment takes place even after discontinuation of drugs in contrast to Polyoxidonium and Amixin treatment methods which require refresher treatment course in order to maintain the result.

The effect attained on composition administration is persistent and lasts for 2 years. Resolution of cosmetic problems in such period makes it possible to improve quality of life and social adaptation of a patient.

Composition does not have any contraindications or side effects and can be administered to a wide range of vitiligo-patients without limitations as well as to patients with concomitant and confounding pathologies.

Since each of composition amino acids is introduced in quantity 3-10 times less than its daily requirement its administration does not provoke any allergic or toxic reactions typical of various vitiligo treatment methods. Moreover there is no danger of squamous cell skin carcinoma, melanoma, cataract, and photoageing.

Composition influence has been tested on a group of 15 patients with vitiligo of spread and bounded form. Patients' age varied from 12 to 31. The group consisted of 9 women and 6 men. Depigmentation focuses were mostly on limbs and body.

Composition was taken 3 times a day in the form of a tablet or powder after tablet porphyrizing sublingually independent of meal in the morning, afternoon and evening. The course took 5 weeks.

Substantial life quality improvement and evident repigmentation can be considered as an effect which was attained by each patient on administration of this composition and lasted for 2 years. There were observed no side effects and complications.

Efficiency of this composition can be demonstrated on the following examples of particular patients.

Example 1

Patient A, 14 years of age diagnosed with vitiligo was under hospital treatment. When she was admitted to hospital there were noticed clear-cut sharply marginated spots on knees, elbows and periorbital region. Composition was administered in accordance with the suggested method.

Composition was administered in the form of a tablet or powder after its porphyrizing 3 times a day for 5 weeks.

Chemistry panel before composition administration: cholesterol—2.2, total bilirubin—4.0, AST (Aspartate aminotransferase)—11.7 u., AlT (Alanine aminotransferase)—7.6 u., gamma GTP (gamma glutamyl transpeptidase)—20.3 mol/l, ALP—111.1 (Alkaline phosphatase) u/l, Trg—0.7 (Triglycerides) mol/l, protein—62.2, glucose—3.1.

Vitiligo-patients suffered no hormonal or biochemical changes. There were noted interleukin IL-1 variations within normal limits There were revealed no side or any adverse effects on administration of the composition.

Amid 5-week composition administration partial repigmentation in depigmentated focuses has been recorded.

The patient was discharged from hospital with significant improvements. The patient's follow-up has shown further pigmentation augment that testifies to intensity and durability of the effect achieved. Administration of composition was repeated in 5 months to nail down the result attained.

Example 2

Patient 26 years of age, vitiligo-patient since 1997. He sought medical attention about vitiligo in December of 2004. First examination showed multiple focuses sized from 1 to 10 cm. in diameter on facial skin, upper and lower limbs.

Concomitant diseases: chronic gastritis, cholangitis, reactive pancreatits, syndrome of vegetative disfunction.

Thyroid ultrasound—norm.

Abdominal ultrasound revealed moderate hepatomegaly with diffusive change of vascular pattern. Moderate diffusive changes of pancreas.

Arterial blood pressure jumps up to 160/100 mmhg

HBs-Ag (test for diagnosis and confirmation of hepatitis C), anti-HCV, IgM k HAV (immunoglobulins to hepatitis A)—none.

Total protein—77, cholesterol—4.6, total bilirubin—13.5, ALP—330, AST—64.2, gamma GTP—2.6, urea—69, creatinine—5.3.

Composition was administered in the form of a tablet or powder after its porphyrizing 3 times a day for 5 weeks. There were noted no side or any adverse effects on administration of composition.

After the first course progression of the process stopped that confirms composition high efficiency. However given process prevalence it was decided to repeat composition administration. After the third course positive dynamics was recorded. Pigment in focuses on facial skin and upper limbs appeared and grew that indicated to efficiency of its impact.

What is claimed is:

1. A method for increasing skin integument repigmentation in vitiligo, said method comprising the steps of sublingually administering an amino acid composition comprising L cystine, L glutamic acid and glycine in the following amounts, mg:

| | |
|---|---|
| L cystine | 85 ± 10%, |
| L glutamic acid | 85 ± 10%, |
| Glycine | 85 ± 10%. |

2. The method according to claim 1, wherein said composition is in the form of a tablet, and the composition further comprises from 1% to 10%, by weight of the tablet, of cellulose ether and from 1% to 10%, by weight of the tablet, of stearate as excipients.

3. A method for increasing skin integument repigmentation in vitiligo, comprising the steps of sublingually administering an amino acid composition 3 times-a-day for a period of 5 weeks, said amino acid composition comprising L cystine, L glutamic acid and glycine in the following quantity, per single dose, mg:

| | |
|---|---|
| L cystine | 85 ± 10%, |
| L glutamic acid | 85 ± 10%, |
| Glycine | 85 ± 10%. |

4. The method according to claim 3, wherein the course of administering the composition is repeated after 4-5 months.

5. The method according to claim 3, wherein the composition is administered in the form of a tablet or a powder obtained by porphyrizing a tablet.

* * * * *